United States Patent [19]

Buck

[11] 4,090,846

[45] May 23, 1978

[54] INDIRECT LATEX TEST FOR DETERMINATION OF FIBRINOGEN DEGRADATION PRODUCTS

[75] Inventor: Francis Fremonte Buck, Suffern, N.Y.

[73] Assignee: Fisher Scientific Company, Pittsburgh, Pa.

[21] Appl. No.: 734,217

[22] Filed: Oct. 20, 1976

[51] Int. Cl.$^2$ .............................................. G01N 33/16
[52] U.S. Cl. .................................... 23/230 B; 424/12; 252/408
[58] Field of Search ......................... 424/12; 23/230 B; 252/408

[56] References Cited

U.S. PATENT DOCUMENTS 3,912,805  10/1975  Cayzer ................................. 424/12
3,915,640  10/1975  Turner ............................. 252/408 X

OTHER PUBLICATIONS

Chemical Abstracts I, 74:61548j (1971).
Chemical Abstracts II, 81:60468r (1974).
Chemical Abstracts III, 81:74190f (1974).
Chemical Abstracts IV, 82:53793k (1975).
Chemical Abstracts V, 83:39746m (1975).

*Primary Examiner*—Sidney Marantz
*Attorney, Agent, or Firm*—Webb, Burden, Robinson & Webb

[57] ABSTRACT

Indirect test for the qualitative and quantitative determination of the presence of fibrinogen degradation products in human serum or urine utilizing the purified D and E fragments of fibrinogen chemically coupled to latex carrier particles as the reagent.

2 Claims, No Drawings

INDIRECT LATEX TEST FOR DETERMINATION OF FIBRINOGEN DEGRADATION PRODUCTS

BACKGROUND OF THE INVENTION

Fibrinogen degradation products (FDP) are usually found in blood as a result of disorders of the coagulation system. They are specifically an indication of a condition known as disseminated intravascular coagulation. They may also be implicated in impending myocardial infarction and the monitoring of their presence may be used as a tool to assess the progress of patients who have suffered from myocardial infarction. Further, their presence in the urine of patients who have received renal transplants is an indication that the transplant is being rejected.

At present there are a variety of tests and kits for analyzing the FDP content of serum and urine. Among such currently available are the following: (A) *Staphylococcal Clumping Test* — Sigma Labs. Reference J. Hawiger, et al., *J. Lab. Clin. Med.*, 75, 93 (1970). This test is based on the fact that a specific strain of Staphylococcus (*Staphylococcus aureus* Newman $D_2C$) will clump in the presence of monomeric fibrin or higher molecular weight FDP. Serial dilutions of samples are mixed with suspensions of the Staphylococcus cells on slides or in test tubes and the presence or absence of clumping noted. This test is non-immunologic in nature; (B) *Fibrinogen Latex Test* — Hyland Labs. This is a direct latex agglutination slide test. Antibodies to human fibrinogen are coupled to latex particles. This test can be used for the detection of FDP because of immunological cross-reactivity but is somewhat lacking in sensitivity; (C) *Hemagglutination-Inhibition Test* — ICL Scientific and Burroughs-Wellcome Co. Reference C. Merskey, et al., *Proc. Soc. Exp. Biol. & Med.*, 131, 871 (1969). This is an indirect type of assay and as such is a two-step method. As generally performed, in the first step, dilutions of the test sample are incubated with a dilute solution of antibodies to human fibrinogen. In the second step, unreacted antibody (i.e. antibody not inhibited by FDP in the sample) is detected by adding tanned red blood cells coated with human plasma. If agglutination occurs no FDP was presented in the original sample dilution. If no agglutination occurs then the original sample contained sufficient FDP to neutralize the antibody. This technique is time consuming and requires extensive apparatus; and (D) *Thrombo-Wellcotest* — Burroughs Wellcome Co. Reference P. M. Pitcher, *Proc. Int. Soc. on Thrombosis and Haemostasis*, Oslo, p. 282, 1971. (See U.S. Pat. No. 3,912,805.) This method is a direct latex agglutination test performed on a glass slide. The latex particles are coated with antibodies to D and E fragments which react directly with the FDP in the serum.

The above suffer from a variety of deficiencies, as for example the hemagglutination inhibition test (C) requires speciazlized apparatus, precise technique and is time consuming; the staphylococcus clumping test (A) is a non-immunological; test (B) is relatively less sensitive; and test (D) is subject to a high incidence of nonspecific latex agglutination. With regard to test (D), *Thromb. Research*, 2, 23 (1970), reports that sera from 25% of patients with rheumatoid arthritis yielded nonspecific agglutination and in testing urine the number of false positive rose to 50% even among healthy donors.

Diagnostic reagents formed by chemically coupling or combining a serologically determinant material to polymeric carrier particles of varying particle size, including latex particles, are well-known, e.g., U.S. Pat. Nos. 3,882,225; 3,857,931; 3,825,525; 3,639,558; 3,565,987; 3,553,310; 3,407,076; 3,236,732; and 3,096,250; Netherlands Pat. No. 7,201,308; and British Pat. No. 1,257,263. Latex particle-gamma globulin suspensions have been used in the serologic diagnosis of rheumatoid arthritis, *Amerian Journal of Medicine* 21; 888–892 (1956).

SUMMARY OF THE INVENTION

The present invention comprises a method for determining FDP in serum or urine which is superior to the above procedures in that it is quantitative when compared with reference standards of known FDP concentrations; it is indirect and based on the inhibition of the antibody-latex FDP reaction by FDP in the sample; it has an extremely low incidence of false positive results; it is more specific for FDP because it employs purified fibrinogen D and F fragments; and antiserum specific for these fragments is rapid and does not require specialized apparatus. The D and E fragments of fibrinogen are discussed in *Ann. Inst. Pasteur Paris*, 100: 377 (1961).

The invention is specifially concerned with an indirect method for the qualitative and quantitative determination of fibrinogen degradation products in a sample of human serum or urine which comprises mixing a sampe of said serum or urine with antiserum to the purified D & E fragments of human fibrinogen; and adding a FDP-latex reagent containing the purified D & E fragments of human fibrinogen chemically coupled to latex carrier particles to said mixture.

A wide-range of carrier particles may be used in the practice of the invention including those discloed in U.S. Pat. Nos. 3,309,275; 3,551,555; 3,639,558; and 3,857,931. A latex carrier particle size of from about 0.1 to about 2.0 microns is deemed suitable. A most suitable latex carrier particle is the polystyrene particles sold by the Dow Chemical Company in a variety of particle sizes, particularly the 0.79 miron size. Lytron 615, manufactured by the Monsanto Chemical Company, with a particle size of 0.15 to 0.25 microns has also been used.

DETAILED DESCRIPTION OF THE INVENTION

The foregoing will serve to illustrate the invention in more detail.

Preparation of the Reagent

A purified preparation of the D and E fragments of fibrinogen is prepared by subjecting purified human fibrinogen [purified by the method disclosed in *Askiv. Kemi*, 10: 415 (1956) followed by chromatography on 0.5m Agarose ®] to degradation by the proteolytic enzyme plasma followed by chromatography on Sephadex ® G-200 (cross-linked polydextran) or 0.5m Agarose ®. The fractions containing the D and E fragments are pooled. Residual plasmin is inhibited by treatment with the inhibitor tosyl-L-lysine chloroketone (TLCK). Residual TLCK is removed by dialysis. Other enzymes may be used to digest fibrinogen to yield fragments resembling D and E.

The purified D and E fragments are coupled to polystyrene latex particles as follows:

A 1.5 to 3 mg. portion of FDP (the purified D & E fractions) in 3 ml. of a buffer, composed of 0.05m glycine, 0.15 sodium chloride and 0.02% sodium azide at pH 8.2, is mixed with 1 ml. of a 10% suspension of latex and 1 ml. of a solution of 40 mg./ml. of 1-ethyl-3(3-dimethylaminopropyl)-carbodiimide hydrochloride in water and the mixture is heated for 10–15 minutes at 55° C. The reaction mixture is cooled and centrifuged. The latex is washed several times with a buffer composed of 0.01m phosphate, 0.15m sodium chloride, 0.02% sodium azide at pH 7.0. The latex is then suspended in a concentration of 1% in this buffer containing 0.02% sodium taurocholate and 0.02% of the surfactant Triton ® X-100.

The latex employed here is sold by Dow Diagnostics and has an average particle diameter of 0.794 microns with a standard deviation of 0.0044 microns.

Performance of the Test

The test is performed on a glass slide containing a multiple number of ovals (usually 3). In the first step, a drop of a dilution of the sample (serum or urine) to be tested is placed in each oval together with a drop of antiserum to FDP. (This antiserum to D and E fragments is produced in rabbits by standard procedures and is prediluted appropriately for the test). The antiserum and sample are mixed for about 30 seconds with an applicator stick and then by rotating the slide. In the second step, a drop of the FDP-latex reagent is added to each previously mixed preparation of sample and antiserum, mixed with an applicator stick and the whole mixture is swirled by rotating the glass slide for 2 minutes. The absence of agglutination of the latex particles indicates that fibrinogen degradation products are present in the sample at the dilution tested (the FDP inhibits the antibody from reacting with the FDP-latex). If agglutination (clumping) of the latex particles occurs, the presence of FDP in the sample is excluded since the uninhibited antibody is free to react with the FDP-latex reagent.

By applying this test serially to different dilutions of the sample to be tested, a quantitative determination can be made of the amount of FDP present in the sample by comparison with reference standards of known concentrations of FDP.

A sample of serum is run in the test system (1:200 dilution of rabbit anti-FDP) alone and after the addition of an aliquot of a preparation of FDP (purified D and E fragments) sufficient to make the serum up to a concentration of 22 micrograms per milliliter with respect to FDP. The test results are as follows:

| Dilution of Serum | Test Result (Agglutination) | Dilution of Serum + FDP | Test Result (Agglutination) |
| --- | --- | --- | --- |
| no dilution | + | no dilution | − |
| 1:2 | + | 1:2 | − |
| 1:5 | + | 1:5 | − |
|  |  | 1:10 | + |

By dilution analysis it is apparent that the system is capable of detecting 4.4 µg./ml. or less of FDP but not as little as 2.2 µg./ml. On average the test system sensitivity is 3.3 µg./ml.

Two unknown samples of serum are run in the test system. The result are as follows:

| Dilution of Serum Sample | Agglutination | |
| --- | --- | --- |
|  | Serum No. 1 | Serum No. 2 |
| no dilution | + | − |
| 1:2 | + | − |
| 1:4 | + | + |

By comparison to the reference standard, unknown serum No. 1 contains less than 3.3 µg./ml. Serum No. 2 contains 3.3 µg./ml. times dilution factor three or 9.9 µg./ml.

With experience, it is possible for a technical operator to distinguish "partial" agglutination reactions from full agglutination reactions and thereby make better quantitative estimations of FDP concentration.

The method of the present invention is suitable for packaging into a diagnostic reagent test kit containing as the essential components thereof a FDP-latex reagent; predilution concentrations of antibody solution; and reference standards containing known amounts of FDP.

I claim:

1. A method for the determination of fibrinogen degradation products in a sample of human serum or urine which comprises mixing a sample of said serum or urine with antiserum to the D and E fragments of human fibrinogen; and adding a FDP-latex reagent containing the D and E fragmens of human fibrinogen chemically coupled to latex particles to said mixture.

2. A method according to claim 1, which comprises applying said method serially to different dilutions of the sample and comparing with reference standards of known concentrations of FDP.

* * * * *